US009267904B2

(12) United States Patent
Lee et al.

(10) Patent No.: US 9,267,904 B2
(45) Date of Patent: Feb. 23, 2016

(54) DEVICE FOR ANALYZING FILM ON SURFACE OF ELECTRODE FOR RECHARGEABLE LITHIUM BATTERY AND METHOD OF ANALYZING FILM ON SURFACE OF ELECTRODE FOR RECHARGEABLE LITHIUM BATTERY USING SAME

(75) Inventors: Seon-Hong Lee, Yongin-si (KR); Ho-Gon You, Yongin-si (KR); Joo-Han Song, Yongin-si (KR); In-Ho Jung, Yongin-si (KR); Jake Kim, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 536 days.

(21) Appl. No.: 13/597,229

(22) Filed: Aug. 28, 2012

(65) Prior Publication Data
US 2013/0287173 A1 Oct. 31, 2013

(30) Foreign Application Priority Data

Apr. 30, 2012 (KR) ........................ 10-2012-0045475

(51) Int. Cl.
*G01T 1/36* (2006.01)
*G01N 23/227* (2006.01)
(Continued)

(52) U.S. Cl.
CPC ............. *G01N 23/2273* (2013.01); *H01J 37/28* (2013.01); *H01M 4/13* (2013.01); *H01M 10/42* (2013.01)

(58) Field of Classification Search
CPC ................ G01N 23/2273; G01N 1/28; G01N 2035/00277; H01J 2237/2005; H01J 49/0409; H01J 37/28; H01M 10/42; H01M 4/13
See application file for complete search history.

(56) References Cited

U.S. PATENT DOCUMENTS 5,990,476 A * 11/1999 Larson et al. ................. 250/251
8,784,512 B2 * 7/2014 Wadley et al. ............... 29/623.5
(Continued)

FOREIGN PATENT DOCUMENTS

KR  1998-029945       7/1998
KR  10-2011-0079516 A  7/2011
(Continued)

OTHER PUBLICATIONS

Bhattacharya, S., et. al., "A transmission electron microscopy study of crack formation and propagation in electrochemically cycled graphite electrode in lithium-ion cells" Journal of Power Sources 196, 2011.*

(Continued)

*Primary Examiner* — Wyatt Stoffa
(74) *Attorney, Agent, or Firm* — Christie, Parker & Hale, LLP

(57) ABSTRACT

A device for analyzing a film on a surface of an electrode for a rechargeable lithium battery includes: an inert chamber capable of maintaining an inert atmosphere including controlled amounts of moisture and oxygen and including an inner space for pretreating a sample including the film on the surface of the electrode; a first analyzer coupled to the inert chamber through a connection tube, the first analyzer being configured to receive the sample and being configured to provide composition and thickness information of the film; an inert holder configured to be assembled around the sample in the inert chamber and configured to maintain the inert atmosphere around the sample; and a second analyzer mounted with the inert holder therein and configured to provide shape information of the film. A method of analyzing a film on a surface of an electrode using the device is also disclosed.

4 Claims, 26 Drawing Sheets

(51) Int. Cl.
    *H01J 37/28*    (2006.01)
    *H01M 4/13*    (2010.01)
    *H01M 10/42*    (2006.01)

(56) References Cited

U.S. PATENT DOCUMENTS

| | | | |
|---|---|---|---|
| 2009/0061105 A1* | 3/2009 | Fukuzawa et al. | 427/539 |
| 2009/0181304 A1* | 7/2009 | Miyamoto et al. | 429/218.1 |
| 2009/0263726 A1 | 10/2009 | Yamaguchi et al. | |
| 2010/0096566 A1* | 4/2010 | Bristol et al. | 250/492.2 |
| 2010/0209771 A1* | 8/2010 | Shizuka et al. | 429/207 |
| 2010/0294049 A1* | 11/2010 | Kelley et al. | 73/864.83 |
| 2010/0297339 A1* | 11/2010 | Okazaki et al. | 427/77 |
| 2011/0049361 A1* | 3/2011 | Preikszas et al. | 250/306 |
| 2011/0217599 A1* | 9/2011 | Yamamoto et al. | 429/306 |
| 2012/0231345 A1* | 9/2012 | Ogawa et al. | 429/304 |
| 2013/0022861 A1* | 1/2013 | Miyagi et al. | 429/163 |
| 2013/0288130 A1* | 10/2013 | Sheem et al. | 429/231.8 |
| 2014/0134461 A1* | 5/2014 | Inoue et al. | 429/7 |

FOREIGN PATENT DOCUMENTS

| | | |
|---|---|---|
| KR | 10-2011-0099878 A | 9/2011 |
| KR | 10-2012-0012628 A | 2/2012 |

OTHER PUBLICATIONS

Bhattacharya, S., et. al., "A transmission electron microscopy study of crack formation and propagation in electrochemically cycled graphite electrode in lithium-ion cells" Journal of Power Sources 196, 2011; pp. 8719-8727.*

Chan, C., et. al., "Surface chemistry and morphology of the solid electrolyte interphase on silicon nanowire lithium-ion battery anodes" Journal of Power Sciences 189 (2009) 1132-1140.*

Bhattacharya, Sandeep et al., A transmission electron microscopy study of crack formation and propagation in electrochemically cycled graphite electrode in lithium-ion cells; Journal of Power Sources 196; 2011; pp. 8719-8727; Elsevier B.V.

Jeong, Soon-Ki et al., Surface film formation on a graphite negative electrode in lithium-ion batteries: AFM study on the effects of co-solvents in ethylene carbonate-based solutions; Electrochimica Acta 47; 2002; pp. 1975-1982; Elsevier Science Ltd.

Jeong, Soon-Ki et al., Interfacial reactions between graphite electrodes and propylene carbonate-based solutions: Electrolyte-concentration dependence of electrochemical lithium intercalation reaction; Journal of Power Sources 175; 2008; pp. 540-546; Elsevier B.V.

Jeong, Soon-Ki, Mechanism of Surface Film Formation of Graphite Negative Electrodes and its Correction with Electrolyte in Lithium Secondary Batteries; Journal of the Korean Electrochemical Society; 2010; vol. 13, No. 1, pp. 19-33.

* cited by examiner

DEVICE FOR ANALYZING FILM ON SURFACE OF ELECTRODE FOR RECHARGEABLE LITHIUM BATTERY AND METHOD OF ANALYZING FILM ON SURFACE OF ELECTRODE FOR RECHARGEABLE LITHIUM BATTERY USING SAME

CROSS-REFERENCE TO RELATED APPLICATION

This application claims priority to and the benefit of Korean Patent Application No. 10-2012-0045475 filed in the Korean Intellectual Property Office on Apr. 30, 2012, the entire contents of which are incorporated herein by reference.

BACKGROUND

1. Field

This disclosure relates to a device for analyzing a film on a surface of an electrode for a rechargeable lithium battery and a method of analyzing a film on a surface of an electrode for a rechargeable lithium battery using the same.

2. Description of the Related Art

Since portable electronic devices have been recently propagated, a rechargeable lithium battery having a high energy density and output voltage is highly required and has drawn more attention. The rechargeable lithium battery has relatively well satisfied the demands as compared to other batteries, so far.

During charging and discharging a rechargeable lithium battery, a film is provided on a surface of an electrode. In other words, an organic solvent of the electrolyte is decomposed on the interface between the electrode and the electrolyte to provide a passivation film (hereinafter referred to 'SEI film') or SEI (solid Electrolyte Interface) on the surface of the electrode.

Since the electrochemical characteristics of rechargeable lithium battery are significantly affected by the film formed on the surface of electrode, it is very important to accurately analyze the film condition. Conventionally, a film on a surface of an electrode for a rechargeable lithium battery is analyzed using any one of a transmission electron microscope (TEM), an atomic force microscope (AFM), and a field emission scanning electron microscope (FE-SEM).

The transmission electron microscope (TEM) provides a transmission image obtained under the high accelerating voltage condition of several hundred kiloelectron volt (keV), but pretreating and observing a sample consumes much time. The SEI film is an organic-inorganic composite layer and has an irregular shape, so the thickness measured in a local region (in several ten to several hundred nanometer scale) is difficult to estimate the thickness of entire film. In addition, pretreatment under the high accelerating voltage damages an organic material, deteriorating the reliability of the measurement.

The atomic force microscope (AFM) provides a surface image and may measure a thickness. However, the technical know-how is very specialized or highly required, and too much time is required for the analysis. In addition, a cantilever is applied in a contact mode, so the cantilever tip is worried to wear off during observing the thickness; in addition, it may not analyze the composition, and it may not be confirmed whether the SEI film is completely removed.

Also, the electric field emission scanning electron microscope (FE-SEM) usually provides a bulk low-magnified image using a high accelerating voltage (greater than or equal to 10 kV), so the definite monitoring for the surface shape is difficult.

SUMMARY

One aspect of the present invention is to provide a device for analyzing a film on a surface of an electrode for a rechargeable lithium battery which may analyze a shape, thickness and composition of a film at a high accuracy within a short time and without damaging the film during the pretreatment process.

Another aspect of the present invention is to provide a method of analyzing a film on a surface of an electrode for a rechargeable lithium battery using the device for analyzing a film.

According to one embodiment, a device for analyzing a film on a surface of an electrode for a rechargeable lithium battery includes an inert chamber capable of maintaining an inert atmosphere including controlled amounts of moisture and oxygen and having an inner space for pretreating a sample including the film on the surface of the electrode; a first analyzer coupled to the inert chamber via a connecting tube (e.g., a connection tube), the first analyzer being configured to receive the sample and being configured to provide composition and thickness information of the film; an inert holder configured to be assembled around the sample in the inert chamber and configured to maintain the inert atmosphere around the sample; and a second analyzer configured to be mounted with the inert holder therein and configured to provide shape information of the film.

The inert chamber may include a chamber main body including a front see-through window; a glove attached to the front see-through; and purifying unit configured to control the amounts of oxygen and moisture in the chamber main body. In one embodiment, the glove is directed toward the inside of the chamber main body.

The purifying unit may include a purifier including a catalyst configured to absorb moisture and oxygen; and a circulating unit configured to send inert gas in the chamber main body to the purifier and configured to provide inert gas passed through the purifier into the chamber main body.

The connecting tube may be coupled to the chamber main body and the connection tube is configured to maintain the same inert atmosphere in the connection tube as in the chamber main body.

The inert atmosphere may have moisture in an amount in a range of 0 ppm to about 0.1 ppm and oxygen in an amount in a range of 0 ppm to about 0.5 ppm.

The first analyzer may be an X-ray Photoelectron Spectrometer (XPS) equipment.

The first analyzer may include an ion gun positioned to have a tilted angle relative to the surface of the sample and the ion gun be configured to emit an ion beam to the film.

The ion beam may have an accelerating voltage in a range of about 0.3 kV to about 0.5 kV and a current condition in a range of about 0.2 μA to about 0.5 μA, and the ion gun may be configured to emit the ion beam until the electrode material under the film approaches to about 50 to about 70 atom % based on the total amount (atomic ratio) of the electrode material prior to the emission of the ion beam.

The second analyzer may be an ultra high resolution electron scanning microscope (XHR-SEM) and configured to emit an electron beam having an accelerating voltage in a range of about 0.5 kV to about 1.0 kV and a current condition in a range of about 1 pA to about 15 pA.

According to another embodiment, a method of analyzing a film on a surface of an electrode for a rechargeable lithium battery is provided that includes pretreating a sample including the film on the surface of the electrode in an inert chamber and controlling the amount of moisture and oxygen in an inert atmosphere in the inert chamber; transporting the sample into a first analyzer to obtain composition and thickness information of the film in the first analyzer; transporting the sample into the inert chamber and assembling an inert holder around the sample in the inert chamber; and transporting the inert holder to a second analyzer to obtain shape information of the film in the second analyzer.

The pretreating the sample may include obtaining the electrode by disassembling the rechargeable lithium battery; cutting the electrode to provide a sample including the film; cleaning the sample; and combining the sample with a supporting substrate or the inert holder.

The transporting the sample into the first analyzer may include transporting the sample through a connecting tube (e.g., a connection tube) between the inert chamber and the first analyzer, and the inert atmosphere of the inert chamber and the connecting tube may have moisture in a range of 0 ppm to about 0.1 ppm and oxygen in a range of 0 ppm to about 0.5 ppm.

The first analyzer may be an X-ray Photoelectron Spectrometer (XPS) equipment; and the second analyzer may be an ultra high resolution scanning electron microscope.

The method may further include ion-etching the sample in the first analyzer before transporting the sample to the inert chamber.

During the ion-etching process, an ion beam having a tilted angle of about 45 to about 60 degree relative to the surface of the sample is emitted, and the ion beam may have an accelerating voltage in a range of about 0.3 kV to about 0.5 kV and a current condition in a range of about 0.2 μA to about 0.5 μA.

The ion-etching may be performed until the electrode material under the film approaches about 50 to about 70 atom % based on the total amount (atomic ratio) of the electrode material prior to the ion etching.

The second analyzer may emit an electron beam having an accelerating voltage in a range of about 0.5 kV to about 1.0 kV and a current condition in a range of about 1 pA to about 15 pA.

Hereinafter, further embodiments of the present invention will be described in more detail.

The film is prevented from damage (or the amount of damage is reduced) during all processes from the pretreatment of the sample to the measurement, so the reliability of the analysis is enhanced. In addition, the shape and composition characteristics may be analyzed in a short time and at a high precision to help the development of a rechargeable battery.

BRIEF DESCRIPTION OF THE DRAWINGS

The accompanying drawings, together with the specification, illustrate exemplary embodiments of the present invention, and, together with the description, serve to explain the principles of the present invention.

DETAILED DESCRIPTION

This invention will be described more fully hereinafter with reference to the accompanying drawings, in which exemplary embodiments of the present invention are shown. This invention may, however, be embodied in many different forms and should not be construed as limited to the exemplary embodiments set forth herein.

The device for analyzing a film according to one embodiment may be used for analyzing a film formed on the surface of electrode for a rechargeable lithium battery.

The rechargeable lithium battery includes a negative electrode, a positive electrode, and an electrolyte providing a transport passage of lithium ions between the negative electrode and the positive electrode, and generates electrical energy by the oxidation and reduction reaction when lithium ion is intercalated/deintercalated in the positive electrode and the negative electrode. The negative electrode includes carbon material, for example, graphite, coke, synthesis carbon, and so on; the positive electrode includes transition metal oxide.

During the charge and discharge process of rechargeable lithium battery, a passivation film known as SEI (Solid Electrolyte Interface; hereinafter referred as 'SEI film') is formed on the surface of the negative electrode and the surface of the positive electrode.

Since the SEI film is an insulator to electrons and a conductor to ions, it should be formed to be sufficiently thick and uniform. When the SEI film is produced early at the initial state of charge and discharge, the internal resistance of the electrode is decreased, and the non-reversible capacity of cycle is improved to improve the cycle-life.

In addition, when a metallic element as a heteroatom is used together with a carbonaceous material as the negative active material, the SEI film formed on the negative electrode acts as an electron acceptor to stabilize the potential of surface of negative electrode, and as a result, lithium may be intercalated/deintercalated at a higher potential.

As in the above, since the electrochemical characteristic of a rechargeable lithium battery is significantly affected by the film on the surface of the electrode, the film status, such as the composition, thickness, and shape, is definitely analyzed to be utilized for the research and development references of a rechargeable lithium battery. Particularly, the SEI film is an organic-inorganic composite layer having an irregular surface shape, so the precise analysis of that film is very important.

The device for analyzing a film according to one embodiment prevents or reduces damage to the film during all processes from the pretreatment of sample to the measurement, so as to increase the reliability of the analysis. In addition, the device may provide ultra high resolution image information and may also provide accurate composition and thickness information of the film obtained from the image information.

Figure 1:
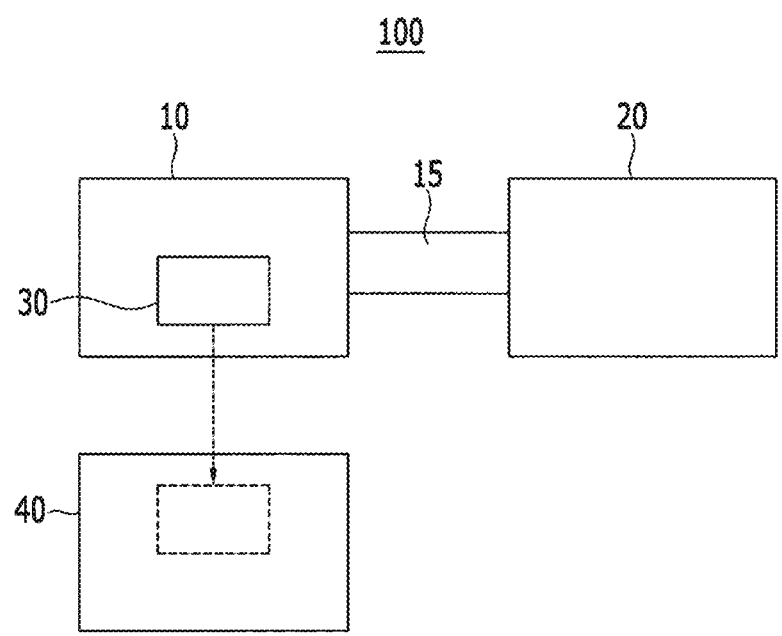
FIG. 1 is a schematic diagram showing a device for analyzing a film on a surface of an electrode for a rechargeable lithium battery.

FIG. 1 is a schematic diagram showing a device for analyzing a film on a surface of an electrode for a rechargeable lithium battery according to one embodiment.

Referring to FIG. 1, the device for analyzing a film 100 according to one embodiment includes an inert chamber 10, a first analyzer 20, an inert holder 30, and a second analyzer 40 and includes a connection tube 15 connecting (or coupling) the inert chamber 10 with the first analyzer 20. The sample is pretreated in the inert chamber 10, and an inert atmosphere is maintained during all processes of transporting the sample toward the first analyzer 20 and the second analyzer 40 and analyzing the film in the first and the second analyzers.

The inert chamber 10 is a chamber capable of maintaining an inert atmosphere, thereby controlling the amount of moisture and oxygen, and the sample to be formed with a film on the surface of the electrode is pretreated therein. The pretreating the sample includes obtaining an electrode by disassembling a rechargeable lithium battery; cutting the electrode into a predetermined or preselected size to provide a sample of electrode formed with a film; cleaning the sample; and displacing the same on a supporting substrate or the inert holder.

The inert chamber 10 may be a glove box.

Figure 2:
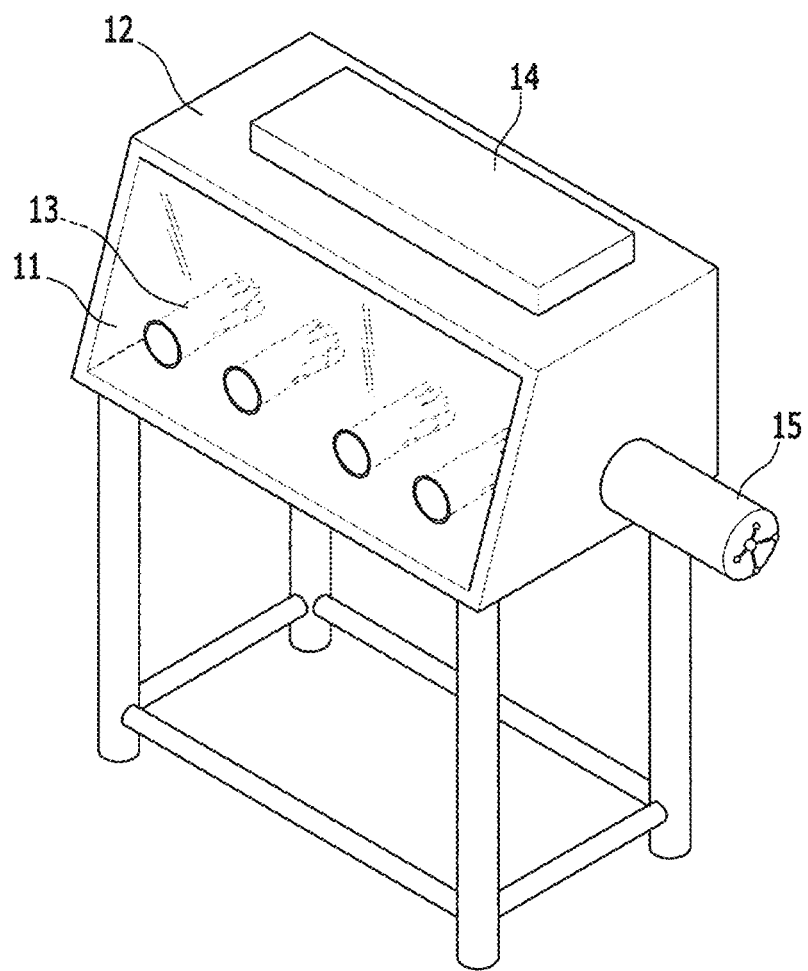
FIG. 2 is a perspective view schematically showing an inert chamber of the device for analyzing a film shown in FIG. 1.

FIG. 2 is a perspective view schematically showing an inert chamber 10 of the device analyzing a film shown in FIG. 1.

Referring to FIG. 2, the inert chamber 10 includes a chamber main body 12 formed with a front see-through window 11; a glove (or gloves) 13 disposed on the front see-through window 11 toward the inside of chamber main body 12; a purifying unit 14 controlling the amount of oxygen and moisture in the chamber main body 12; and a connection tube 15 disposed on one side of the chamber main body 12.

The glove 13 is made of flexible material such as butylene rubber so as to make the movement of worker's hands smooth.

The purifying unit 14 maintains the continuous inert atmosphere by substituting nitrogen or argon gas in the chamber main body 12. The purifying unit 14 may include a purifier, a circulation unit, and a gas control unit.

The purifier includes a catalyst absorbing moisture and oxygen. The catalyst may be and is not limited to platinum, silica, zeolite, or the like. The circulation unit sends nitrogen or argon gas in the chamber main body 12 into the purifier and supplies the gas passed through the purifier into the chamber main body 12 again to decrease the amount of moisture and oxygen in the chamber main body 12. The gas control unit controls all gases for purifying the chamber main body 12.

The connection tube 15 is an auxiliary chamber for transporting the sample to maintain the same inert atmosphere as in the chamber main body 12. The connection tube 15 is connected (or coupled) to the first analyzer 20 and supplies the sample pretreated from the chamber main body 12 to the first analyzer 20 while maintaining the inert atmosphere.

The inert chamber 10 may maintain the concentration of moisture in the atmosphere in a range of 0 ppm to about 0.1 ppm and oxygen 0 ppm to about 0.5 ppm. The film on a surface of an electrode for a rechargeable lithium battery is rapidly reacted with moisture and oxygen when exposed to air and spoiled (or damaged). Accordingly, when the amounts of moisture and oxygen of the inert chamber 10 are within the above ranges, the film damage may be prevented or reduced during the pretreatment process, so the reliability of the analysis may be enhanced.

Referring to FIG. 1, again, the first analyzer 20 is connected (or coupled) to the inert chamber 10 by the connection tube 15 and receives the sample, and provides information on the surface composition of the film and the thickness of the film by the depth profile. The first analyzer 20 includes an X-ray Photoelectron Spectrometer (XPS).

Figure 3:
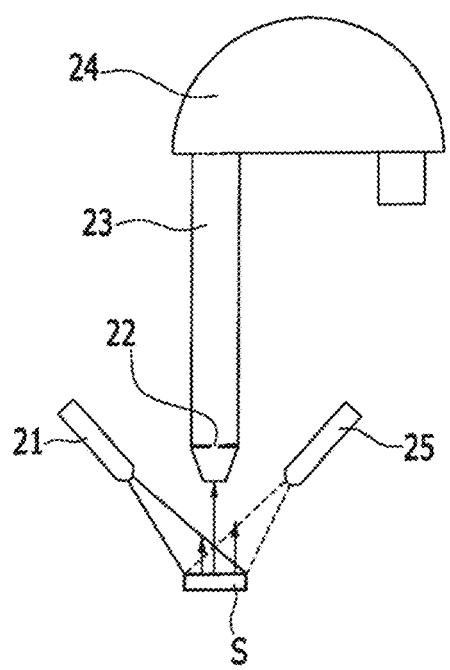
FIG. 3 is a schematic diagram showing a first analyzer of the device for analyzing a film shown in FIG. 1.

FIG. 3 is a schematic diagram showing the first analyzer in the device for analyzing a film shown in FIG. 1.

Referring to FIG. 3, the first analyzer 20 includes an X-ray generator 21 and an analyzer 24 including a slit 22 and an electromagnetic lens region 23. When the X-ray generator 21 irradiates x-rays toward the sample, the sample S receives X-rays having high energy and generates photoelectrons. The photoelectrons pass through the narrow slit 22 and propagate through the electromagnetic lens region 23, and the analyzer 24 analyzes the photoelectrons to provide information regarding the surface of the sample S.

The first analyzer 20 provides the surface composition information of a micro region having one face of several nm to several tens of nm and also provides the thickness information of the film by the depth profile. Accordingly, the film composition and thickness may be precisely analyzed using the first analyzer 20.

The first analyzer 20 may be also used as ion etching equipment. Ion etching is one step of pretreatment for analyzing the film and preparing the film to provide 3D image information from the film in the second analyzer 40. In FIG. 3, 25 refers to an ion gun. The ion gun 25 is displaced to have a predetermined or preselected tilted angle to the surface of the sample S, for example, about 45° to about 60° and emits an inert ion beam to the film.

The ion etching (XPS etching) using the first analyzer 20 satisfies the condition of accelerating voltage in a range of about 0.3 kV to about 0.5 kV and the current condition in a range of about 0.2 µA to about 0.5 µA. The organic components of SEI film may be thermally deformed by collision with accelerated ions or may be easily damaged by surface oxidation/reduction reactions. When the accelerating voltage of the ion beam is within the above range, the damage to the film's organic component may be minimized or reduced; the efficiency of ion etching is enhanced; the etching time is shortened; and the reaction time with fine carbon impurity in the inert chamber is not long, so that the film may be prevented from contamination or the amount of contamination may be reduced.

The accelerating voltage of the ion beam for the XPS etching is significantly lower as compared other etching processes, such as focused ion beam (FIB) etching and CP (cross section polisher) etching as shown in the following Table 1.

TABLE 1

| | Accelerating voltage |
|---|---|
| Focused ion beam (FIB) etching | 20-30 kV |
| CP etching | 6-8 kV |
| XPS etching | 0.3-0.5 kV |

Focused ion beam (FIB) etching and CP etching probably damage the film due to heat damage from the high voltage of the ion beam. However, the ion etching (XPS etching) using the first analyzer 20 has significantly low accelerating voltage for the ion beam, as compared to FIB etching and CP etching, so damage to the film may be minimized or reduced.

Referring to FIG. 1 again, the first analyzer 20 is connected (or coupled) to the inert chamber 10 through the connection tube 15 and receives a sample under the inert atmosphere. Additionally, the second analyzer 40 maintains the inert atmosphere using the inert holder 30 when transporting the same.

The inert holder 30 provides space for mounting the sample in the inside thereof and has a closed and sealed structure for blocking air inflow by closely sealing around the sample. The inert holder 30 is assembled with the sample in the inert chamber 10 and maintains an inert atmosphere around the sample. The inert holder 30 is not limited to a certain structure and may be applied to any structure as long as it has a space for mounting the sample and it is capable of maintaining the closed and sealed structure.

The second analyzer 40 is mounted with the inert holder 30 therein and analyzes the surface shape and cross-sectional shape of the film and provides 3D image information based on the surface and cross-section image. The second analyzer 40 includes an ultra high resolution scanning electron microscope. The scanning electron microscope is a device for observing the image obtained from electrons reflected from the sample surface after scanning an electron beam spot on the surface of the sample.

Figure 4:
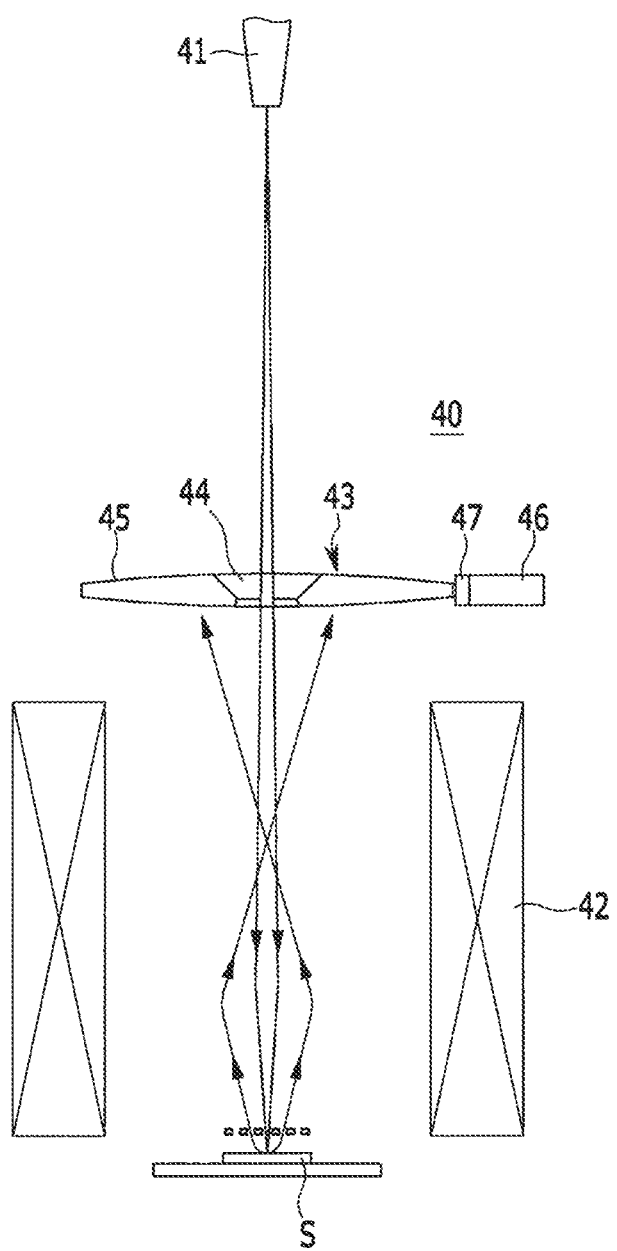
FIG. 4 is a schematic diagram showing a second analyzer of the device for analyzing a film shown in FIG. 1.

FIG. 4 is a schematic diagram of a second analyzer 40 in the device for analyzing a film shown in FIG. 1.

Referring to FIG. 4, the second analyzer 40 includes an electron gun 41 emitting an electron beam and irradiating the same to a sample S; an object lens 42 including a coil to focus the electron beam on the sample S; and a secondary electron detector 43 for detecting secondary electrons generated from the sample S where the electron beam was irradiated.

The secondary electron detector 43 includes a disk 45 forming a through-hole 44 for passing the electron beam and generating protons by receiving secondary electrons; a proton amplifying tube 46 disposed outside of the disk 45 and detecting protons generated in the disk 45; and a light guide 47 disposed between the disk 45 and the proton amplifying tube 46. The second analyzer 40 shown in FIG. 4 shows only one exemplary structure, but the inside structure of the second analyzer 40 is not limited thereto.

The second analyzer 40 has an ultra high resolution in a range of about 0.9 nm to about 1 nm at about 1.0 kV and satisfies the condition of having an accelerating voltage in a range of about 0.5 kV to about 1.0 kV and the current condition in a range of about 1 pA to about 15 pA. When satisfying the accelerating voltage and current conditions within the above ranges, accurate observations may be performed for the SEI film because the secondary electron range emitted from the surface is equal to or less than the thickness of SEI film.

By using the second analyzer 40, the surface shape of an ultra micro region having one side of several nm to several tens nm may be easily observed based on the high resolution achieved under the low accelerating voltage. For example, the surface shape and cross-sectional shape of the film may be observed using the second analyzer, and the 3D-shape of the film may be analyzed based on the surface and cross-section images.

Hereinafter, a method of analyzing a film on a surface of an electrode for a rechargeable lithium battery using the device for analyzing a film 100 is described.

Figure 5:
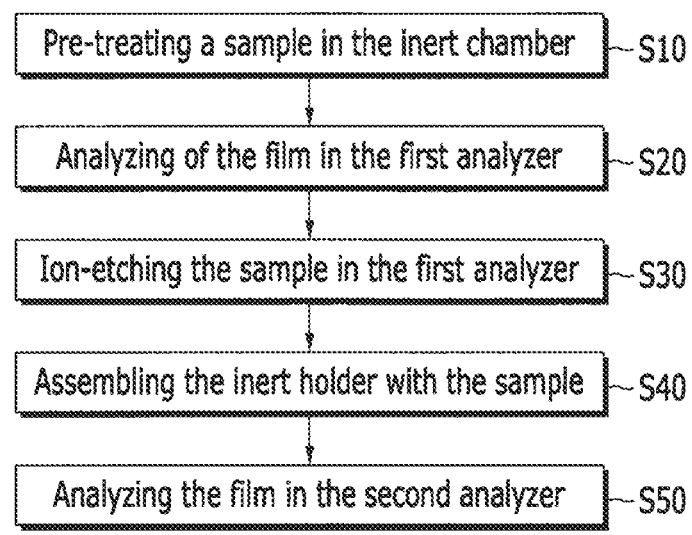
FIG. 5 is a flow chart showing a method of analyzing a film on a surface of an electrode for a rechargeable lithium battery according to one embodiment.

FIG. 5 is a flow chart showing a method of analyzing a film on a surface of an electrode for a rechargeable lithium battery according to one embodiment.

Referring to FIG. 5, a method of analyzing a film includes a first step of pretreating a sample in the inert chamber (S10); a second step of transporting the sample to a first analyzer and analyzing the film in the first analyzer (S20); a third step of ion-etching the sample in the first analyzer (S30); a fourth step of transporting the sample into the inert chamber and assembling the inert holder with the sample in the inert chamber (S40); and a fifth step of mounting the inert holder in the second analyzer and analyzing the film in the second analyzer (S50).

In the first step S10, pretreating the sample includes disassembling a rechargeable lithium battery; cutting an electrode into a predetermined or preselected size to provide an electrode sample formed with a film; cleaning the sample; and mounting the sample on a supporting substrate or the inert holder. The supporting substrate plays a role in supporting the sample in the first analyzer.

The inert chamber 10 may maintain an atmosphere having a moisture concentration in a range of about 0 ppm to about 0.1 ppm and oxygen of 0 ppm to about 0.5 ppm. Since the sample is pretreated in the inert chamber 10, the reaction of the film with moisture and oxygen in air is blocked or reduced to prevent the film from being spoiled or damaged, or to reduce the damage to the film.

In order to evaluate the film status of the sample pretreated in the inert chamber 10, the following tests are performed.

EXAMPLE 1 AND REFERENCE EXAMPLES 1 AND 2

$LiNi_2Co_5Mn_3O_2$, carbon black and polyvinylidene fluoride were mixed at a weight ratio of 90:5:5, respectively, to provide a positive active material slurry, and the slurry was coated on an aluminum foil and dried and pressed to provide a positive electrode. Natural graphite/artificial graphite (at a weight ratio of 6:4), carbon black, and styrene-butadiene rubber (SBR) were mixed at a weight ratio of 98:1:1, respectively, to provide a negative active material slurry, and the slurry was coated on a copper foil and dried and pressed to provide a negative electrode. The obtained positive electrode and negative electrode and a separator of polyethylene/polypropylene material were wound and compressed and inserted into a cylindrical can, and then an electrolyte was injected thereto and sealed to provide a rechargeable lithium battery cell. The electrolyte was prepared by adding fluoroethylene carbonate (FEC) and vinylethylene carbonate (VEC) into a mixed solution (at a volume ratio of 3:5:2) of ethylene carbonate (EC), ethylmethyl carbonate (EMC), and dimethyl carbonate (DMC); and dissolving $LiPF_6$ having a concentration of 1.0 M therein. At this time, the amount of FEC and VEC were 5 parts by weight and 2 parts by weight, respectively, based on 100 parts by weight of the mixed solution.

The obtained rechargeable lithium battery cell was disassembled in the inert chamber 10 to provide a negative electrode, and the negative electrode was cut into a predetermined or preselected size to provide a sample formed with a film on the surface of the negative electrode and washed with dimethyl carbonate (DMC).

In Example 1, the sample was stored in the inert chamber 10 for 10 minutes after washing; in Reference Example 1 and Reference Example 2, the samples were exposed in air for 10 minutes and 240 minutes, respectively, after washing.

Evaluation 1: Analysis of Film Status of Pretreated Sample

Figure 6A:
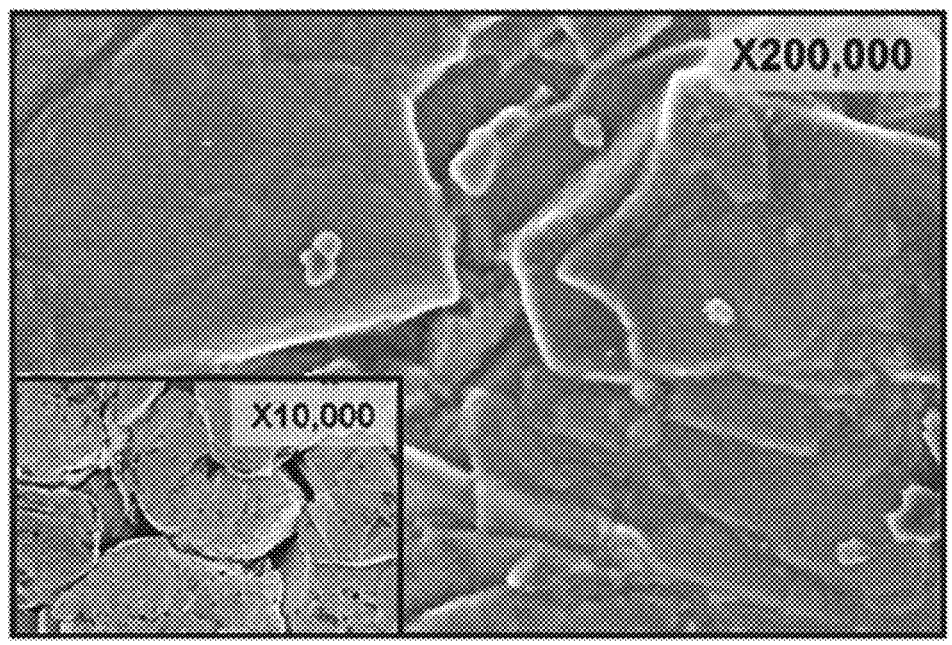
FIG. 6A is a scanning electron microscope photograph showing a film on a surface of an electrode for a rechargeable lithium battery according to Example 1.
Figure 6B:
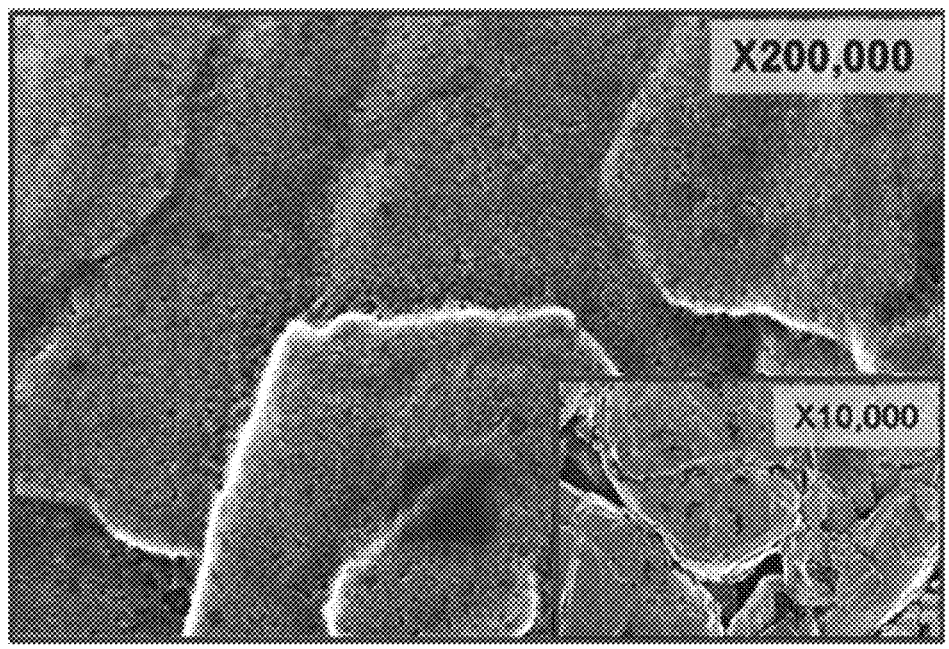
FIG. 6B is a scanning electron microscope photograph showing a film on a surface of an electrode for a rechargeable lithium battery according to Reference Example 1.

FIG. 6A is a scanning electron microscope photograph showing the film on the surface of the electrode for a rechargeable lithium battery according to Example 1; FIG. 6B is a scanning electron microscope photograph showing the film on the surface of the electrode for a rechargeable lithium battery according to Reference Example 1.

As shown in FIG. 6A and FIG. 6B, the film according to Reference Example 1, which was exposed to air, reacted with moisture and oxygen in the air (e.g., atmosphere) and spoiled (e.g., was damaged). In addition, the film according to Reference Example 1 had a rough surface from the damage and spoil, as compared to the film according to Example 1.

Figure 6C:
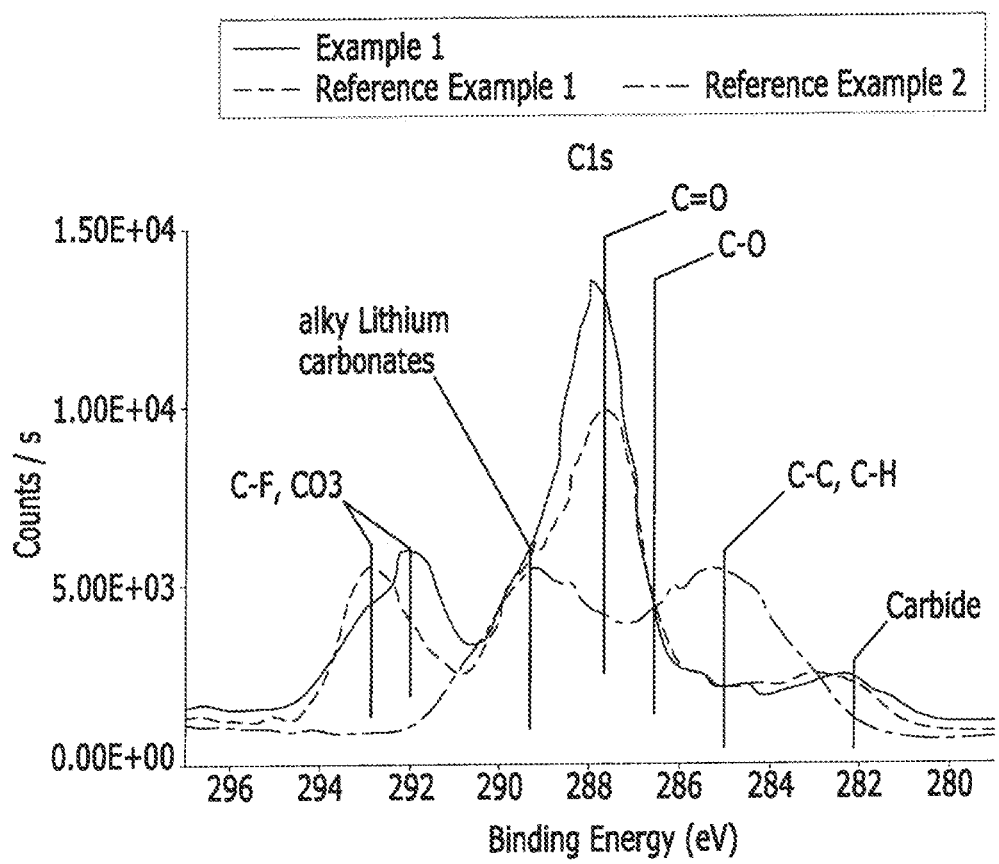
FIG. 6C is a graph showing the change of organic material among film components on the surface of electrode for each rechargeable lithium battery according to Example 1 and Reference Examples 1 and 2.
Figure 6D:
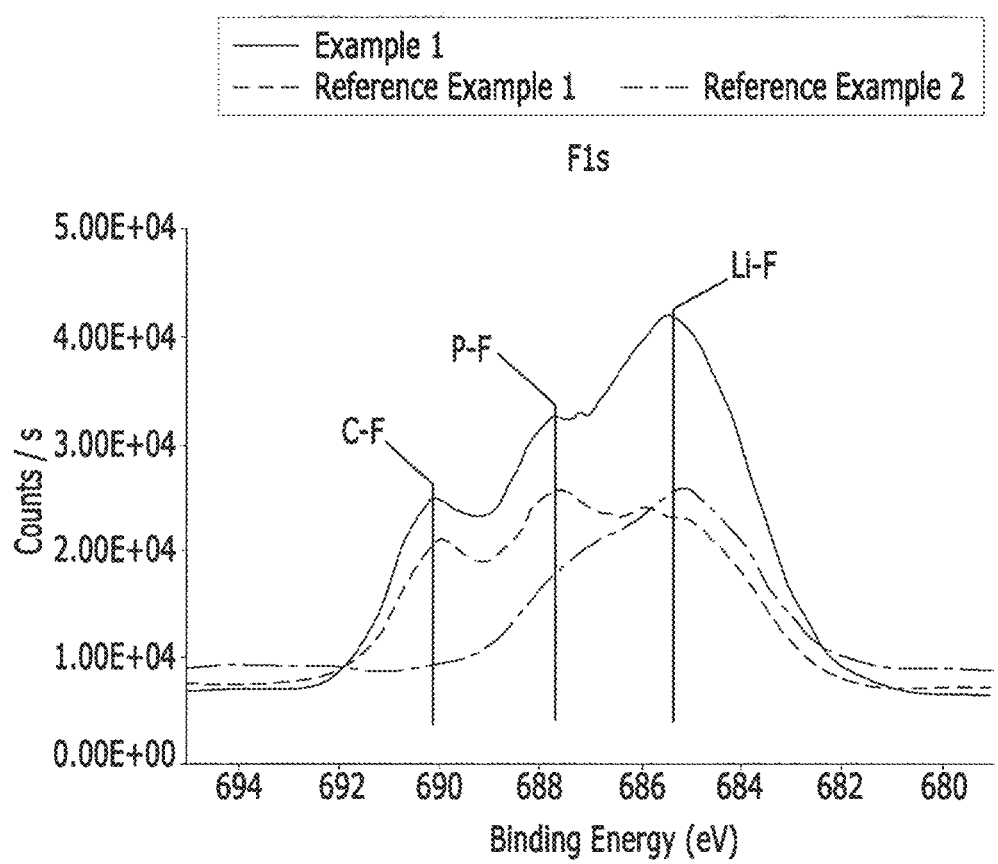
FIG. 6D is a graph showing the change of inorganic material among film components on the surface of electrode for each rechargeable lithium battery according to Example 1 and Reference Examples 1 and 2.

FIG. 6C is a graph showing the change in the organic materials of the components of the film on the surface of each electrode of the rechargeable lithium battery cells according to Example 1 and Reference Examples 1 and 2; FIG. 6D is a graph showing the change in the inorganic materials of the components of the film on the surface of each electrode for the rechargeable lithium battery cells according to Example 1 and Reference Examples 1 and 2

Referring to FIG. 6C and FIG. 6D, it is confirmed that Example 1, which was not exposed to air during pretreatment, had different film components than Reference Examples 1 and 2, which were exposed to air during pretreatment.

In the second step (S20), the sample was provided on the support substrate (not shown) and introduced into the first analyzer 20 through the connection tube 15. In one embodiment, the first analyzer 20 is an X-ray Photoelectron Spectrometer (XPS), and the composition and the thickness of film were analyzed.

In the third step (S30), the sample was ion-etched. The ion-etching of the sample is to analyze the thickness of film and, at the same time, to prepare the film to provide 3D image information of the film from the second analyzer 40, and the ion-etching was performed until deciding the film was completely removed, connecting (or coupling) the depth profiling analysis of first analyzer 20.

Figure 7:
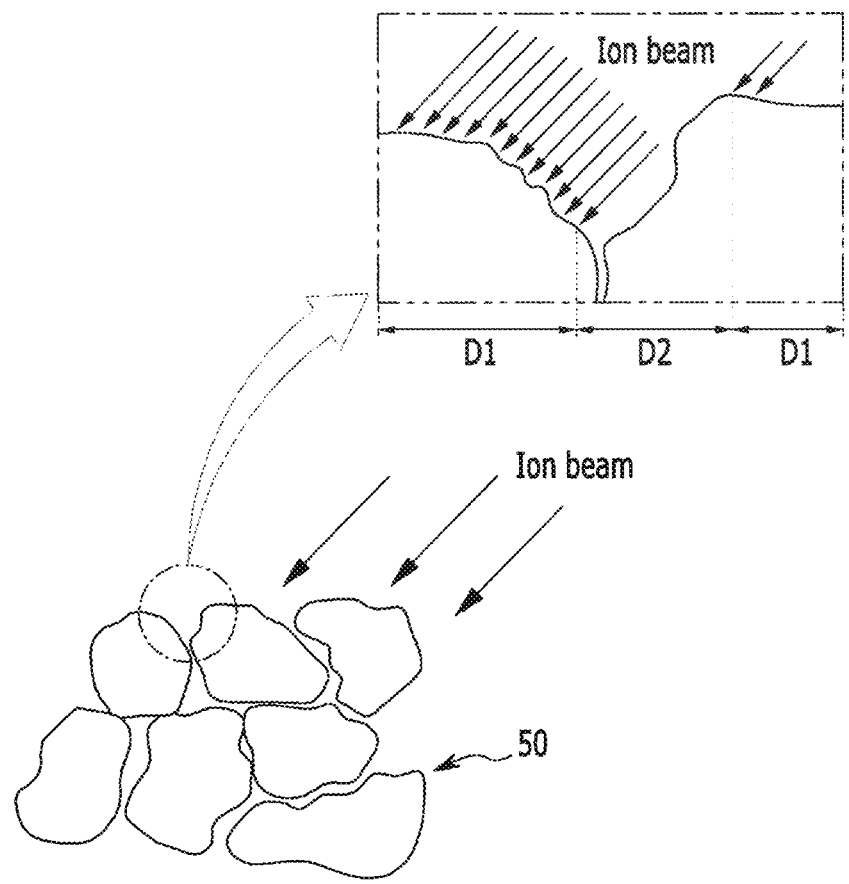
FIG. 7 is a schematic diagram showing ion-etching process using a first analyzer according to one embodiment.

FIG. 7 is a schematic diagram showing ion etching process using the first analyzer according to one embodiment.

Referring to FIG. 7, when an inert ion beam was emitted to the film 50 from an ion gun only a part region of film was exposed with ion beam since the film 50, an organic-inorganic composite layer, had an irregular shape and due to the tilted angle (45 degree to 60 degree) of the ion beam. In FIG. 7, D1 region refers to a region that was exposed to the ion beam; D2 region refers to a region that was not exposed to the ion beam.

Although the ion beam was irradiated to the entire film 50, a shadow region (D2 region) that was not exposed to the ion beam due to the tilted angle of the ion beam was present, so the three dimensional shape of the film 50 may be analyzed by observing the shadow region (D2) of the film 50 using the second analyzer 40.

In one embodiment, the ion-etching (XPS etching) satisfied the conditions of having an accelerating voltage in a range of 0.3 kV to 0.5 kV and a current condition in a range of 0.2 µA to 0.5 µA. When the ion beam had the accelerating voltage within the above range, damage to the film organic component may be prevented or reduced. The ion beam may be emitted until the electrode material under the film, for example, a carbon material, approaches 50 to 70 atom % based on the total amount of electrode material prior to the ion-etching or prior to the emission of the ion beam. In one embodiment, the ion etching time may be determined or preselected.

To confirm the film status depending upon or with respect to the ion etching time, the following tests were performed.

EXAMPLE 2 AND REFERENCE EXAMPLE 3

$LiCoO_2$, carbon black, and polyvinylidene fluoride were mixed at a weight ratio of 90:5:5, respectively, to provide a positive active material slurry, and the slurry was coated on an aluminum foil and dried and pressed to provide a positive electrode. Natural graphite/artificial graphite (at a 6:4 weight ratio), carbon black, and styrene-butadiene rubber (SBR) were mixed at a weight ratio of 90:5:5, respectively, to provide a negative active material slurry, and the slurry was coated on a copper foil and dried and pressed to provide a negative electrode. The obtained positive electrode and negative electrode and a separator of polyethylene/polypropylene material were wound and compressed and inserted into a cylindrical can and injected with an electrolyte and sealed to provide a rechargeable lithium battery cell. The electrolyte was prepared by adding fluoroethylene carbonate (FEC) and vinylethylene carbonate (VEC) into a mixed solution (volume ratio of 3:5:2) of ethylene carbonate (EC), ethylmethyl carbonate (EMC), and dimethyl carbonate (DMC); and dissolving $LiPF_6$ having a concentration of 1.0 M therein. At this time, the amount of FEC and VEC were 5 parts by weight and 2 parts by weight, respectively, based on 100 parts by weight of the mixed solution.

The obtained rechargeable lithium battery was pretreated in the inert chamber 10 to provide a sample including a film on the surface of the negative electrode, and the film was ion-etched in the first analyzer 20.

In the case of Example 2, the electrode material under the film was ion-etched until approaching 60 atom % based on the total amount of electrode material prior to the ion-etching (e.g., prior to the emission of the ion beam); in the case of Reference Example 3, the electrode material under the film was ion-etched until approaching to 80 atom % based on the total amount of electrode material prior to the ion-etching (e.g., prior to the emission of the ion beam).

Evaluation 2: Analysis of Film Composition Depending Upon Ion Etching Time

Figure 8A:
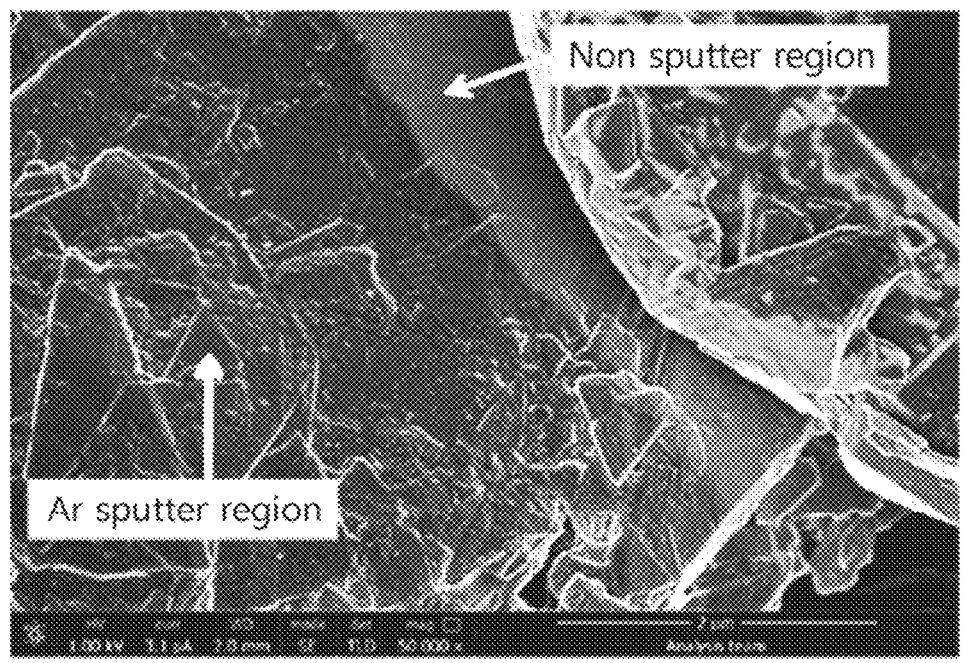
FIG. 8A is a scanning electron microscope photograph showing a film on a surface of an electrode for a rechargeable lithium battery according to Example 2.
Figure 8B:
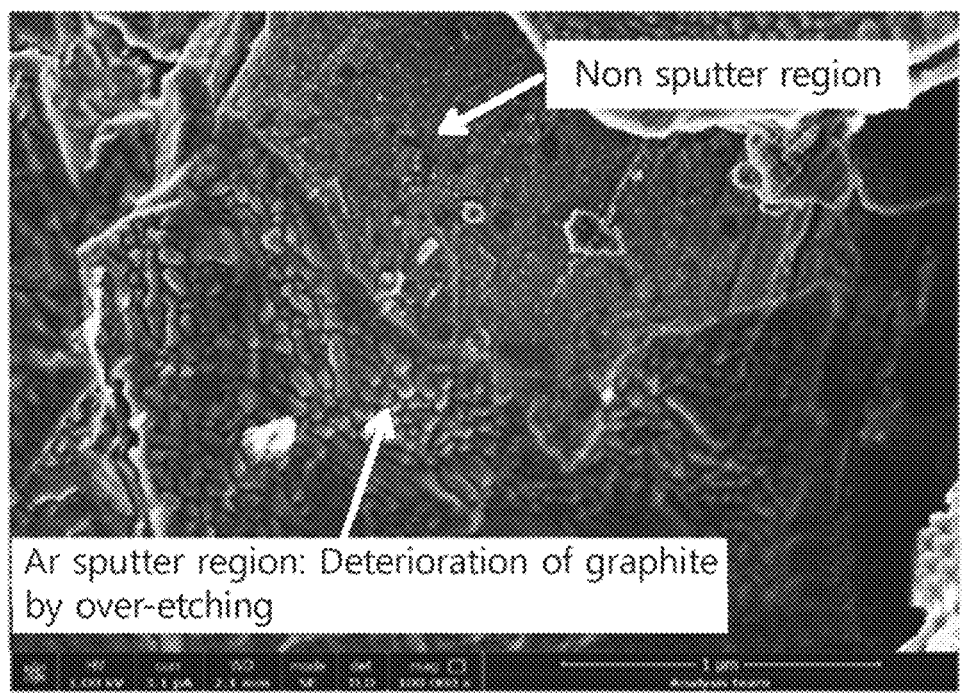
FIG. 8B is a scanning electron microscope photograph showing a film on a surface of an electrode for a rechargeable lithium battery according to Reference Example 3.

FIG. 8A is a scanning electron microscope photograph showing the film on the surface of the electrode for a rechargeable lithium battery according to Example 2; and FIG. 8B is a scanning electron microscope photograph showing the film on the surface of the electrode for a rechargeable lithium battery according to Reference Example 3.

Referring to FIG. 8A and FIG. 8B, when the electrode material under the film was excessively etched, for example, in an amount greater than 70 atom %, it is confirmed that even carbon material under the film was etched, and even graphite was etched as shown in FIG. 8B. The etching time may be appropriately determined within the above-described range according to the composition elements of rechargeable lithium battery and the kind of electrolyte solution.

Figure 8C:
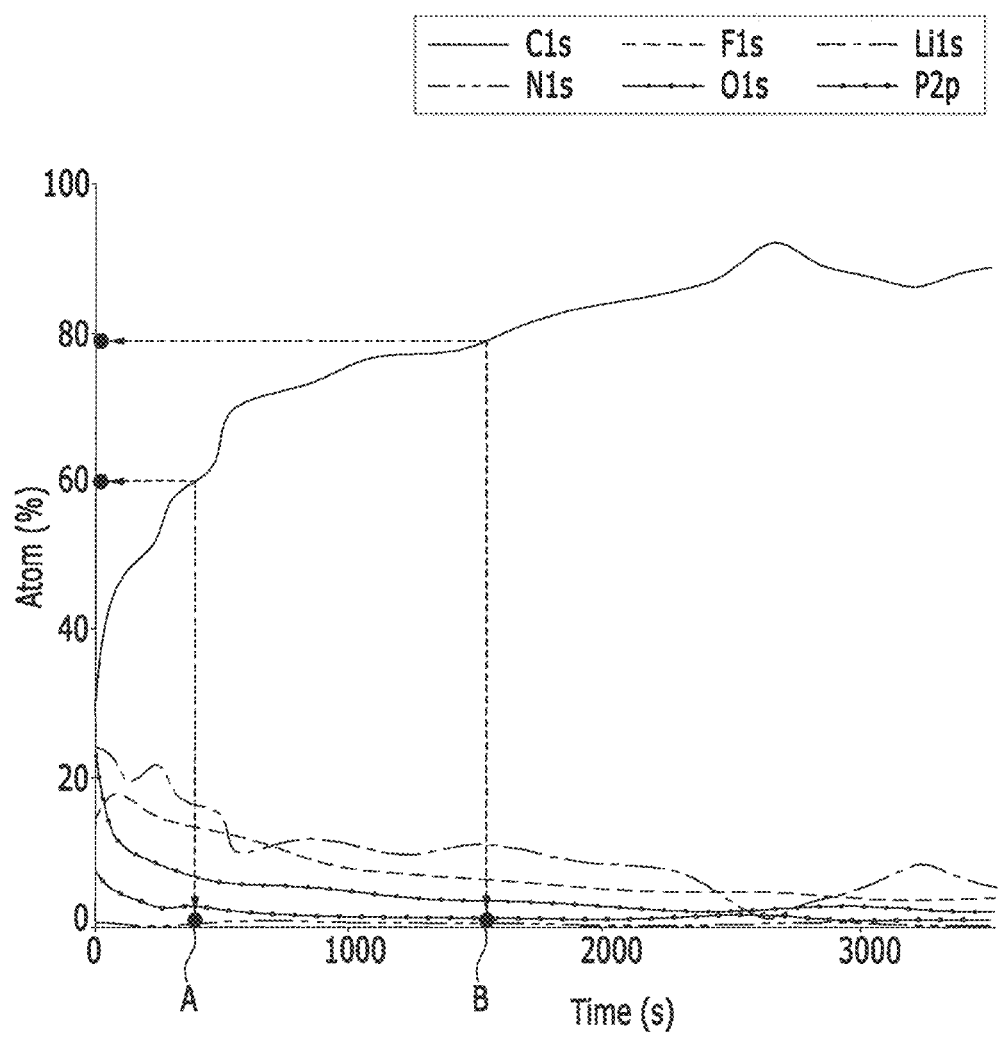
FIG. 8C is a graph showing the change of film components on a surface of an electrode for a rechargeable lithium battery component Example 2 and Reference Example 3.

In addition, FIG. 8C is a graph showing the change of film components on a surface of an electrode for each rechargeable lithium battery according to Example 2 and Reference Example 3.

Referring to FIG. 8C, when the electrode material under the film in Example 2, shown in the region of A, was excessively etched compared to the case of Reference Example 3, shown in the region of B, it is confirmed that even the electrode material under the film was etched to change the composition of the electrode material.

The film composition may be changed according to the charge and discharge state of the rechargeable lithium battery cell.

To confirm the composition change of the film according to the charge and discharge state of the rechargeable lithium battery, it was tested as follows:

Evaluation 3: Analysis of Film Composition According to Charge and Discharge of Battery Cells The rechargeable lithium battery cell according to Example 2 was charged and discharged under the following conditions.

The initial charge was performed in the free charging condition by undergoing at constant current-constant voltage (CC-CV) at 0.5 C and until about 3.5 V, aging at a room temperature (300K) for 24 hours, aging at a high temperature (318K) for 12 hours, and discharging at 0.5 C until about 2.75 V in order to obtain a thin layer at discharge state.

The charged and discharged rechargeable lithium battery was pretreated in the inert chamber 10 to provide a sample including the film on the surface of the negative electrode, and then the film composition was analyzed in the first analyzer 20.

Figure 9A:
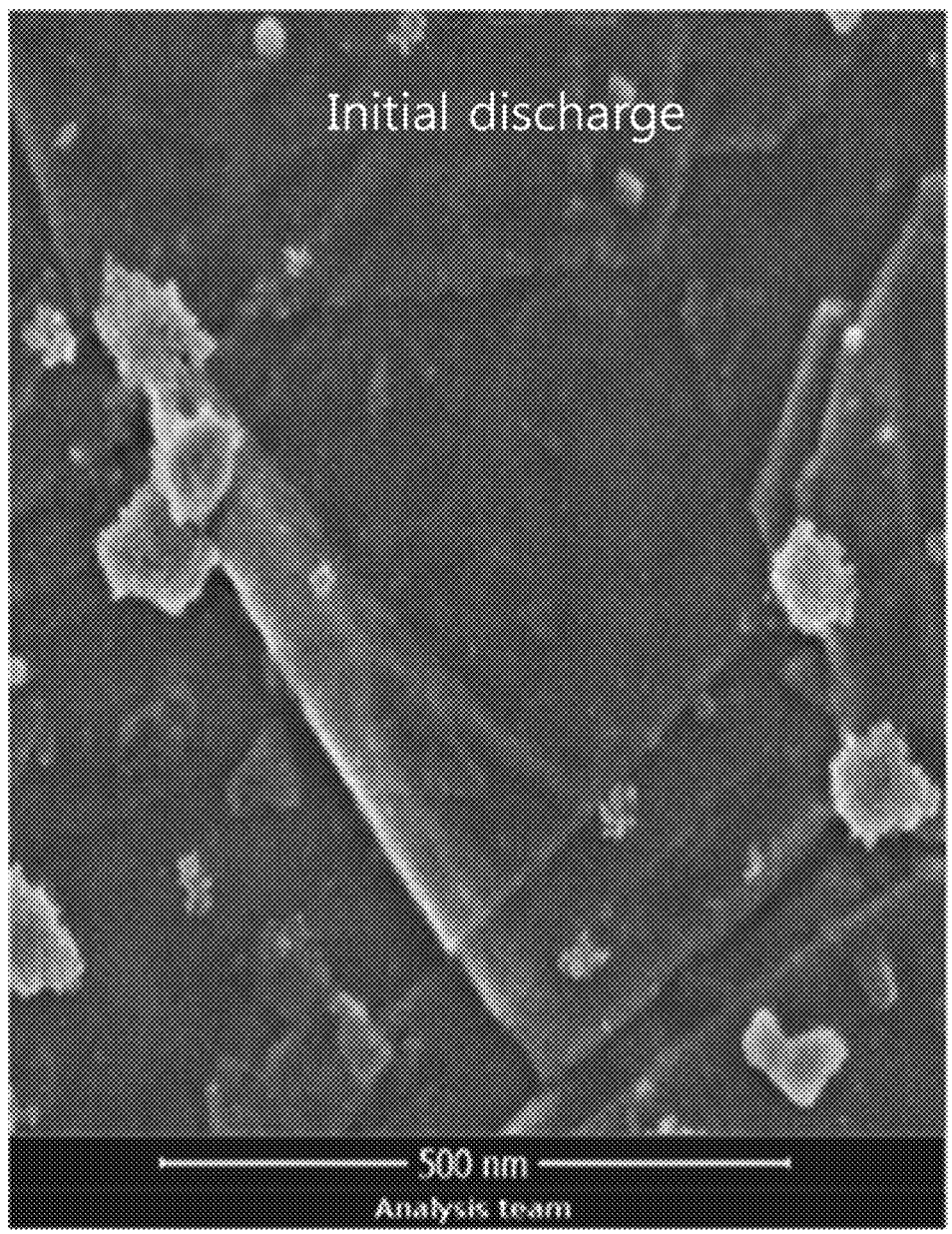
FIG. 9A to FIG. 9C are scanning electron microscope photographs of a film for a rechargeable lithium battery according to Example 2 at the initial discharge, at the initial charge, and at the 300th cycle, respectively.
Figure 9B:
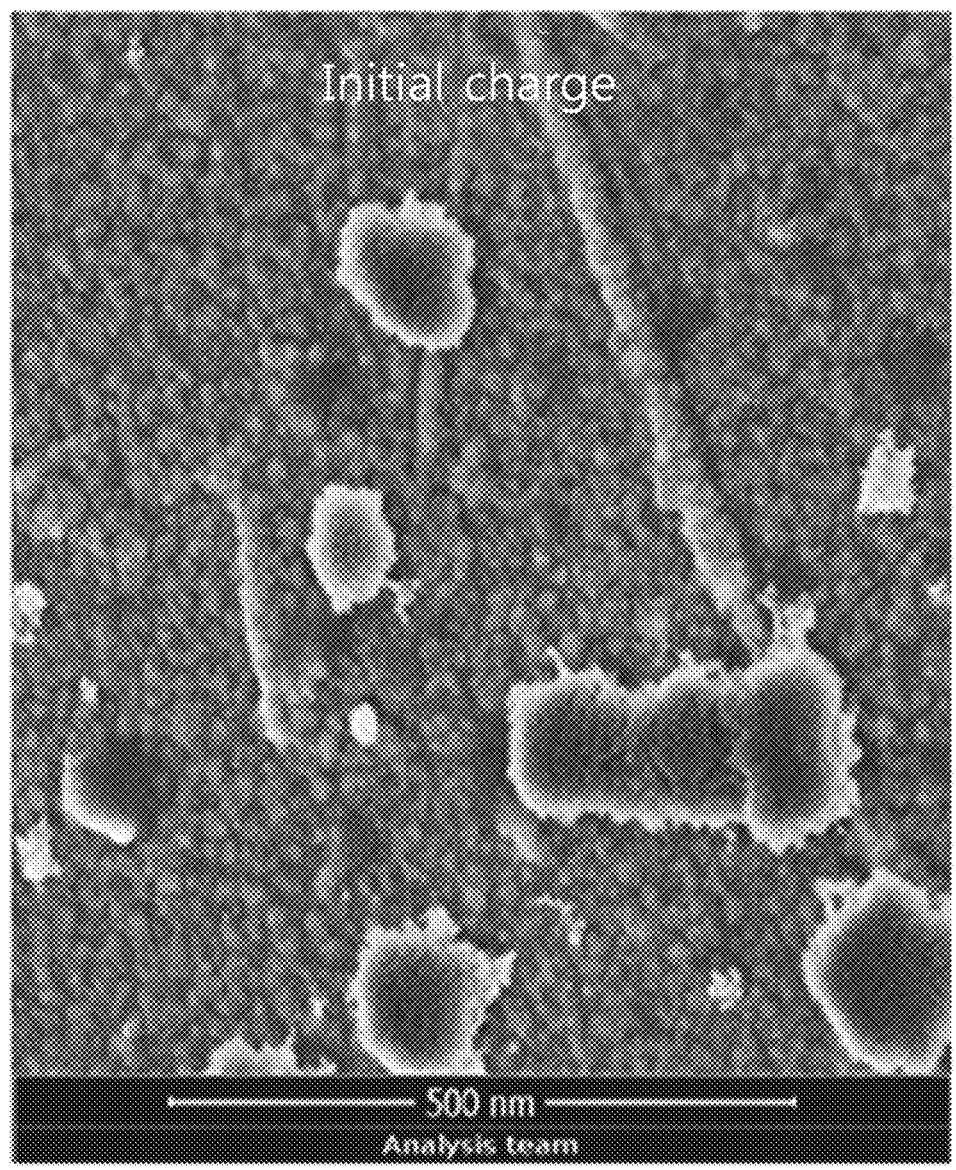
Figure 9C:
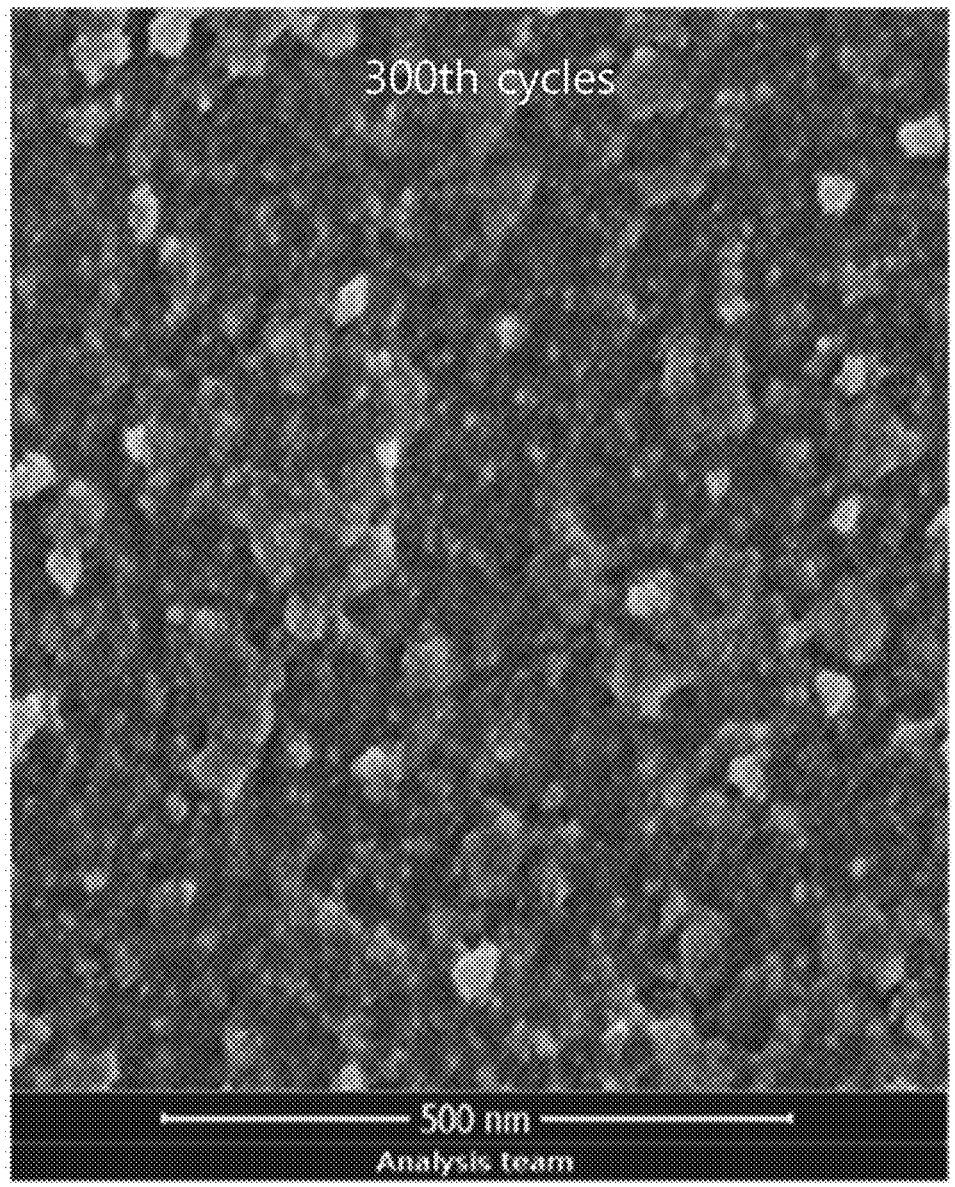

FIG. 9A to FIG. 9C are scanning electron microscope photographs showing the film of the rechargeable lithium battery according to Example 2 at the initial discharge, at the initial charge, and at the 300th cycle, respectively.

Referring to FIG. 9A to FIG. 9C, it is confirmed that the shape of film surface was changed according to the charge and discharge state of the rechargeable lithium battery.

Figure 9D:
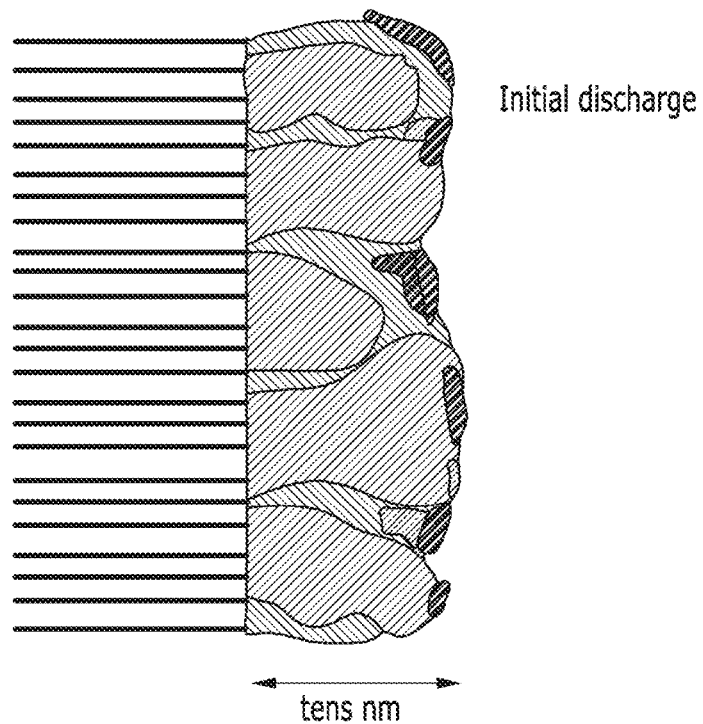
FIG. 9D to 9F are cross-sectional views showing the change of film components for a rechargeable lithium battery according to Example 2 at the initial discharge, at the initial charge, and at the 300th cycle, respectively.
Figure 9E:
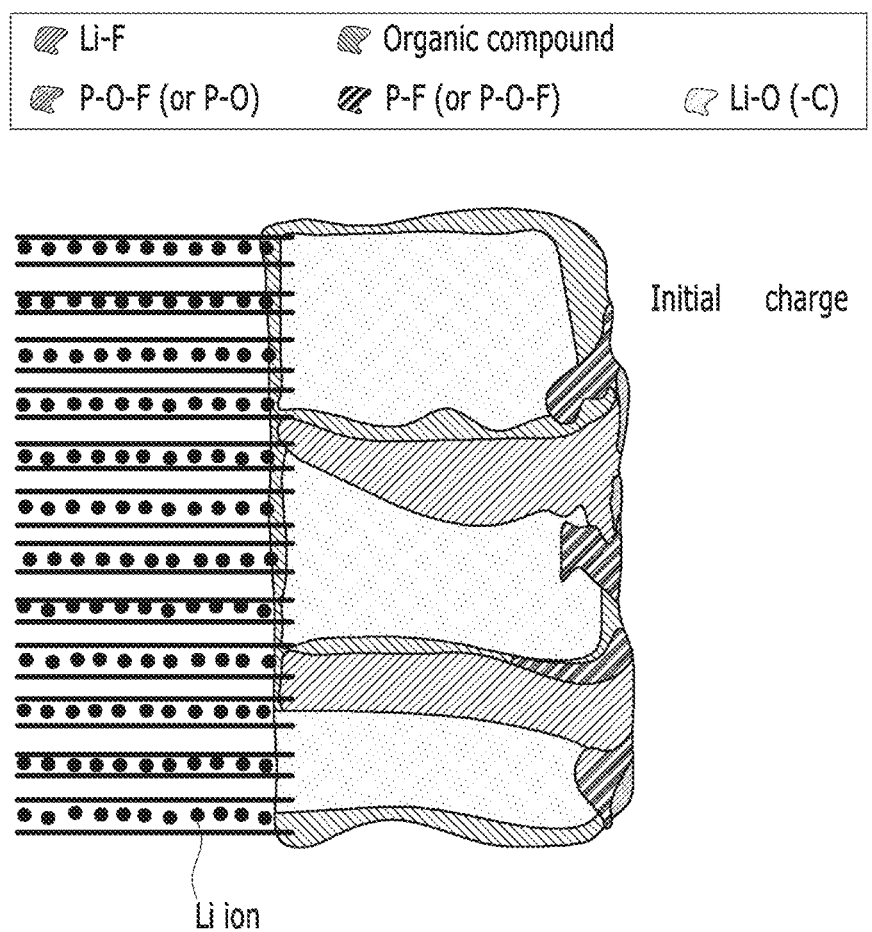
Figure 9F:
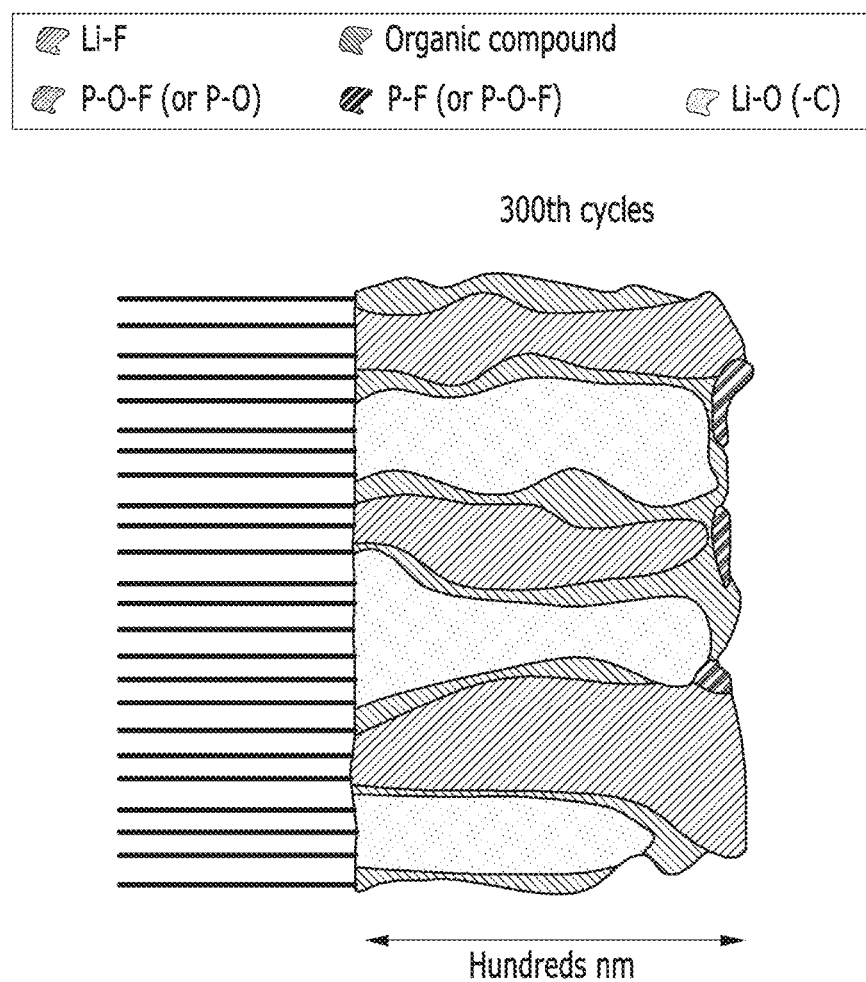

In addition, FIG. 9D to 9F are cross-sectional views showing the film composition change of the rechargeable lithium battery cell according to Example 2 at the initial discharge, at the initial charge, and at the $300^{th}$ cycle, respectively.

Referring to FIG. 9D to 9F, it is confirmed that the composition, the thickness, and the shape of film were changed depending upon the charge and discharge state of the rechargeable lithium battery cell. Thereby, it may be confirmed that the film was different depending upon the charge and discharge state of the rechargeable lithium battery cell, and the film status (e.g., the composition change according to the charge and discharge of the battery) may be analyzed at high precision using the device for analyzing a film according to one embodiment.

In the fourth step (S40), the sample was transported to the inert chamber 10 and assembled with the inert holder 30 in the inert chamber 10.

In the fifth step (S50), the inert holder 30 is mounted in the second analyzer 40, and the surface shape and cross-section shape and 3D image information of film are analyzed using the second analyzer 40. In this embodiment, the second analyzer 40 was an ultra high resolution scanning electron microscope and satisfied the condition of having an accelerating voltage in a range of 0.5 kV to 1.0 kV and a current condition in a range of 1 pA to 15 pA.

In order to confirm the film status according to the accelerating voltage condition in the second analyzer, the following test was performed.

EXAMPLE 3 AND REFERENCE EXAMPLE 4 AND 5

$LiNi_2Co_5Mn_3O_2$, carbon black and polyvinylidene fluoride were mixed at a weight ratio of 90:5:5, respectively, to provide a positive active material slurry, and the slurry was coated on an aluminum foil and dried and compressed to provide a positive electrode. Natural graphite/artificial graphite (at a weight ratio of 6:4), carbon black, and styrene-butadiene rubber (SBR) were mixed at a weight ratio of 90:5:5, respectively, to provide a negative active material slurry, and the slurry was coated on a copper foil and dried and pressed to provide a negative electrode. The obtained positive electrode and negative electrode and a separator of polyethylene/polypropylene material were wound and compressed and inserted into a cylindrical can, and then an electrolyte was injected thereto and sealed to provide a rechargeable lithium battery cell. The electrolyte was prepared by adding fluoroethylene carbonate (FEC) and vinylethylene carbonate (VEC) into a mixed solution (at a volume ratio of 3:5:2) of ethylene carbonate (EC), ethylmethyl carbonate (EMC), and dimethyl carbonate (DMC); and dissolving $LiPF_6$ having a concentration of 1.0 M therein. At this time, the amount of FEC and VEC were 5 parts by weight and 2 parts by weight, respectively, based on 100 parts by weight of the mixed solution.

The obtained rechargeable lithium battery cell was pretreated in the inert chamber 10 to provide a sample including a film on the surface of the negative electrode, and then the film was analyzed in the first analyzer 20 and in the second analyzer 40 mounted within the inert holder 30.

In the case of Example 3, the film was analyzed under the condition of an accelerating voltage of 1 kV in the second analyzer 40; in the case of Reference Examples 4 and 5, the film was analyzed under the condition of an accelerating voltage of 5 kV and 10 kV, respectively, in the second analyzer 40.

Evaluation 4: Analysis of Film Status According to Accelerating Voltage Condition in the Second Analyzer FIG. 10A, FIG. 10B and FIG. 10C are scanning electron microscope photographs showing the film on the surface of the electrode for each rechargeable lithium battery cell according to Example 3, Reference Example 4, and Reference Example 5, respectively.

Figure 10A:
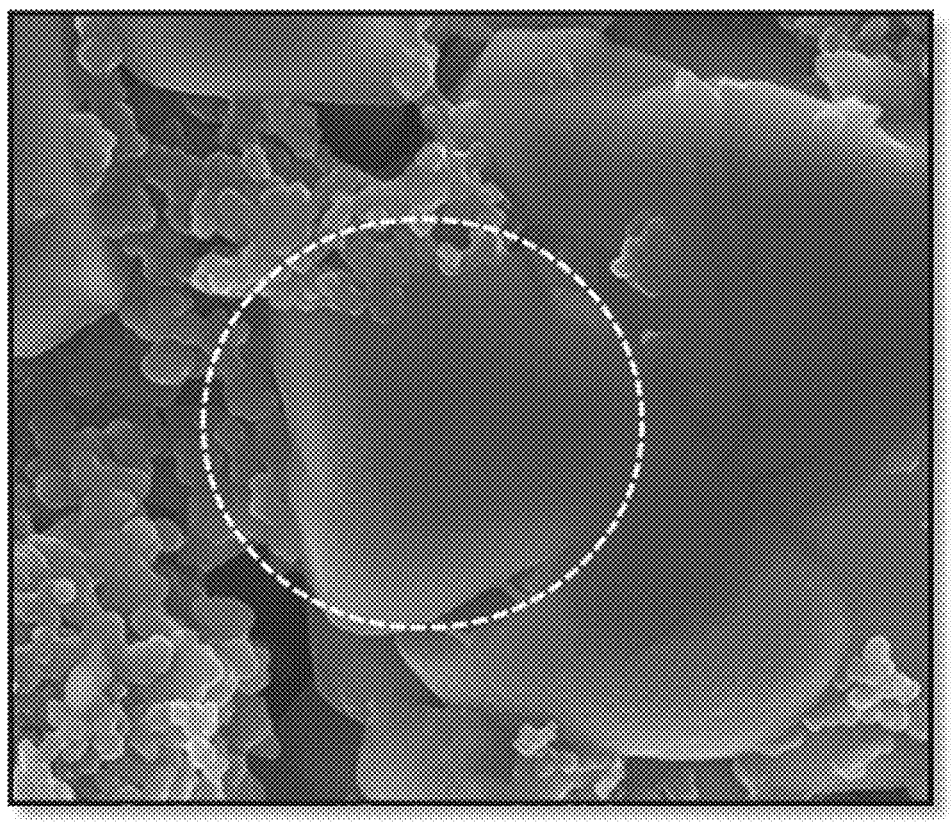
FIG. 10A, FIG. 10B and FIG. 10C are scanning electron microscope photographs showing each film on a surface of an electrode for a rechargeable lithium battery according to Example 3, Reference Example 4 and Reference Example 5, respectively.
Figure 10B:
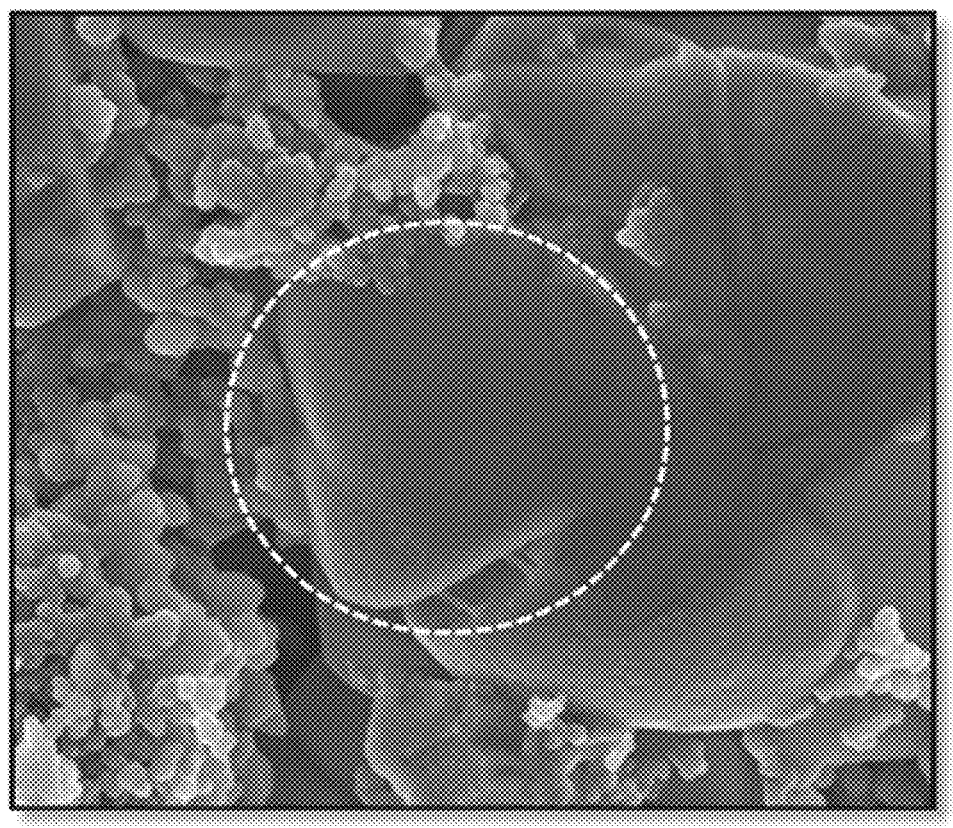
Figure 10C:
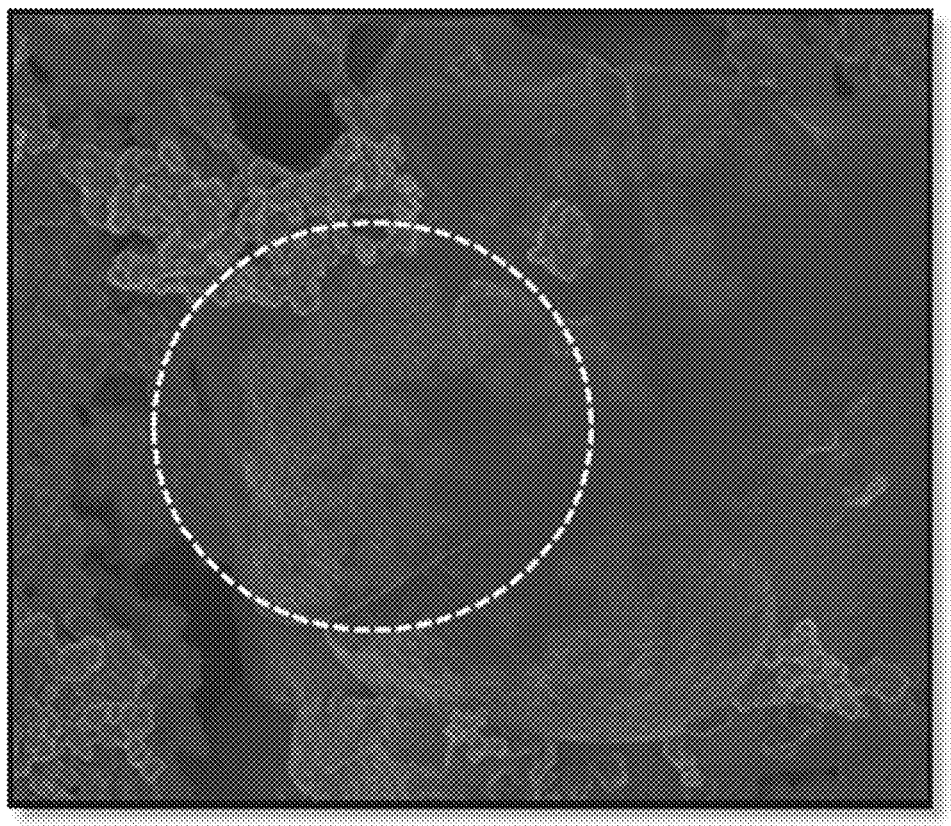

Referring to FIG. 10A to FIG. 10C, it is confirmed that the outermost surface of the film was less precisely shown as the accelerating voltage increased; Example 3 having an accelerating voltage of 1 kV precisely showed the minute surface region, which was not observed in Reference Examples 4 and 5.

In order to confirm the three dimensional shape of film, the following test was performed.

EXAMPLE 4

$LiCoO_2$, carbon black and polyvinylidene fluoride were mixed at a weight ratio of 90:5:5, respectively, to provide a positive active material slurry, and the slurry was coated on an aluminum foil and dried and pressed to provide a positive electrode. Natural graphite/artificial graphite (at a weight ratio of 6:4), carbon black, and styrene-butadiene rubber (SBR) were mixed at a weight ratio of 90:5:5, respectively, to provide a negative active material slurry, and the slurry was coated on a copper foil and dried and pressed to provide a negative electrode. The obtained positive electrode and negative electrode and a separator of polyethylene/polypropylene material were wound and compressed, and inserted into a cylindrical can, and then an electrolyte was injected thereto and sealed to provide a rechargeable lithium battery cell. The electrolyte was prepared by adding fluoroethylene carbonate (FEC) and vinylethylene carbonate (VEC) into a mixed solution (at a volume ratio of 3:5:2) of ethylene carbonate (EC), ethylmethyl carbonate (EMC), and dimethyl carbonate (DMC); and dissolving $LiPF_6$ having a concentration of 1.0 M therein. At this time, the amount of FEC and VEC were 5 parts by weight and 2 parts by weight, respectively, based on 100 parts by weight of the mixed solution.

In the case of Example 4, the obtained rechargeable lithium battery cell was pretreated in the inert chamber 10 to provide a sample including the film on the surface of the negative electrode and analyzed in the first analyzer 20 and in the second analyzer 40 mounted within the inert holder 30.

Evaluation 5: Analysis of 3D Shape of Film

Figure 11A:
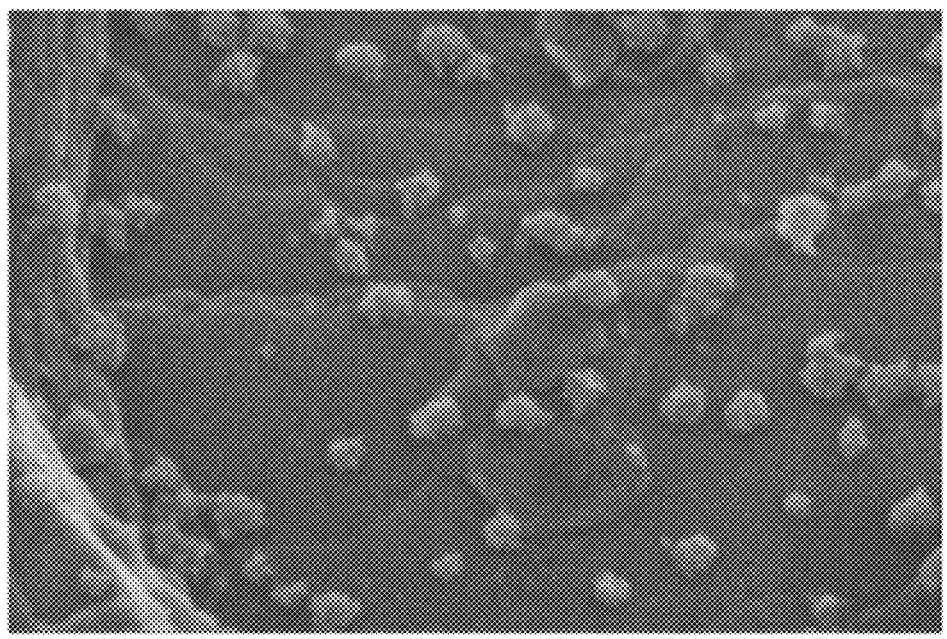
FIG. 11A to FIG. 11D are scanning electron microscope photographs showing the 3-Dimensional shape of a film on a surface of an electrode for a rechargeable lithium battery according to Example 4 depending upon the ion etching degree.
Figure 11B:
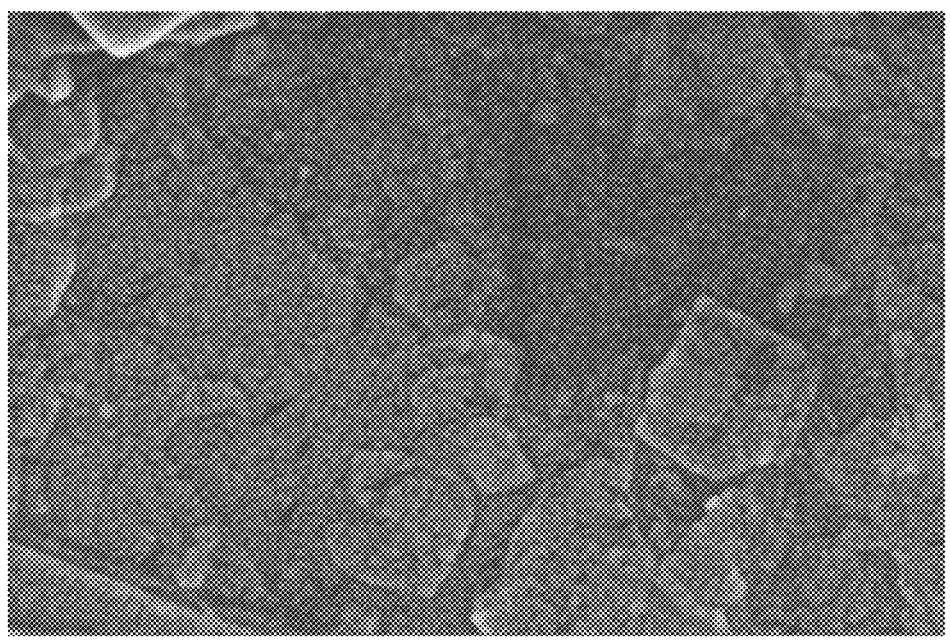
Figure 11C:
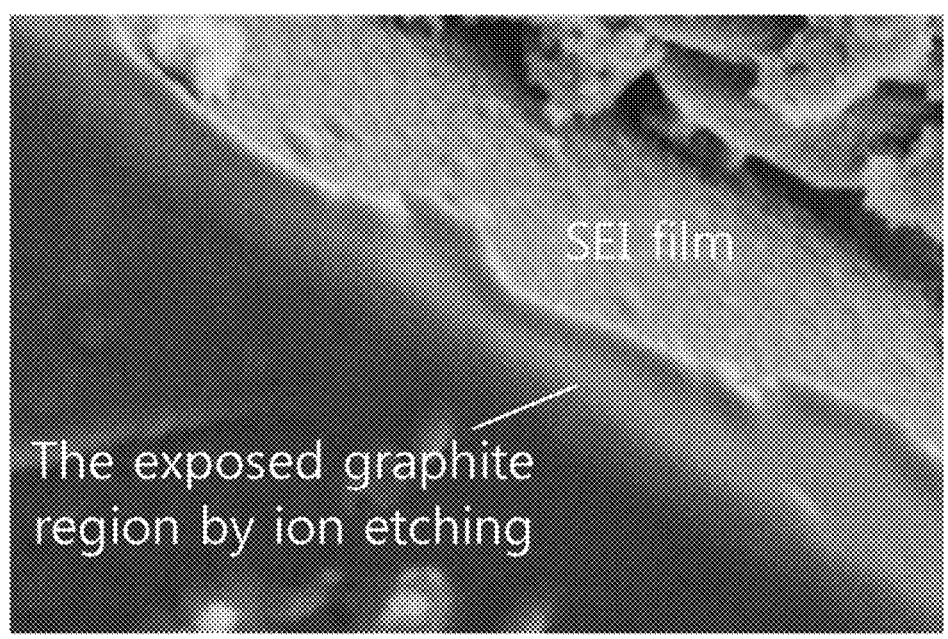
Figure 11D:
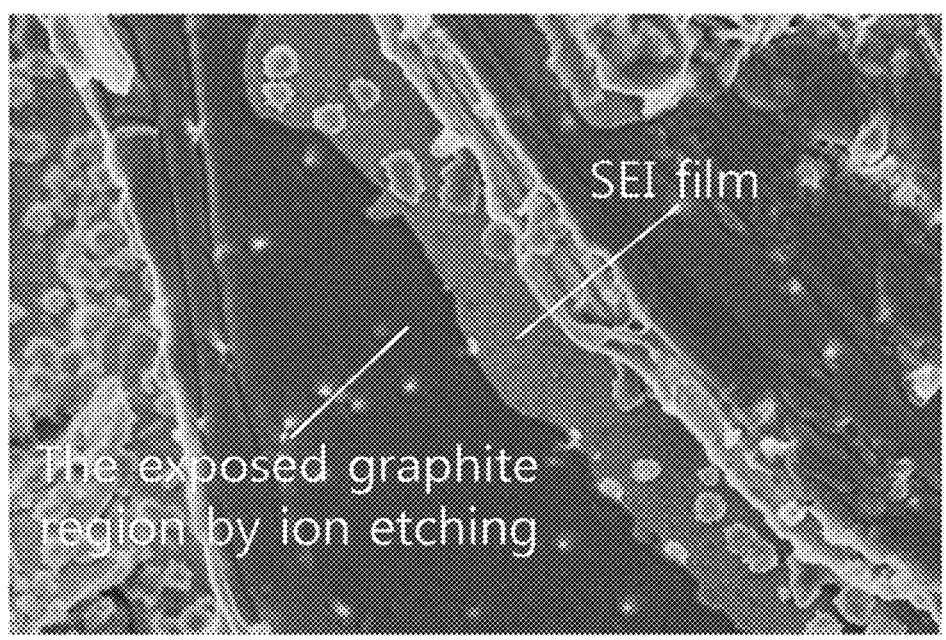

FIG. 11A to FIG. 11D are scanning electron microscope photographs of the film on the surface of the electrode for a rechargeable lithium battery of Example 4 according to the etching degree. For example, FIG. 11A shows the normal SEI film before the ion etching; FIG. 11B shows a partial crack on the SEI film after ion etching; FIG. 11C shows the SEI film and the exposed graphite region after completing the ion etching; and FIG. 11D shows the ultrahigh-magnificationally enlarged step between the exposed graphite shown in FIG. 11C and the non-etched normal SEI film to observe the SEI film thickness.

Referring to FIG. 11A to 11D, the SEI film was gradually cracked by the ion etching and disappeared to expose the electrode material, for example, graphite, under the film. In this case, the shadow region of the film (D2 region in FIG. 7) remained since the ion beam did not contact the shadow region, so the remaining film region was significantly different from the exposed electrode material region. Thereby, the step between the exposed electrode material region and the remaining film region may be distinguished.

According to the method of analyzing a film according to one embodiment, the 3-D surface and cross-sectional surface shape of the film may be observed, and the film may be further analyzed in the multilateral aspect. In addition, it may observe wider and more various regions of the SEI film having very irregular shape, compared to the conventional transmission electron microscope (TEM) and atomic force microscope (AFM).

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. A method of analyzing a film on a surface of an electrode for a rechargeable lithium battery comprising:
    pretreating a sample comprising the film on the surface of the electrode in an inert chamber and controlling the amount of moisture and oxygen in an inert atmosphere in the inert chamber;
    transporting the sample into a first analyzer to obtain composition and thickness information of the film in the first analyzer;
    transporting the sample into the inert chamber and assembling an inert holder around the sample in the inert chamber;
    ion etching the sample in the first analyzer before transporting the sample to the inert chamber; and
    transporting the inert holder to a second analyzer to obtain shape information of the film in the second analyzer,
    wherein the first analyzer is an X-ray Photoelectron Spectrometer (XPS),
    wherein the second analyzer is a high resolution scanning electron microscope,
    wherein an ion beam having a tilted angle relative to the surface of the sample is emitted during the ion etching,
    wherein the ion beam has an accelerating voltage in a range of about 0.3 kV to about 0.5 kV and a current condition in a range of about 0.2 µA to about 0.5 µA, and
    wherein the ion etching is performed until the electrode material under the film approaches about 50 to about 70 atom % based on the total amount of the electrode material prior to the ion etching.

2. The method of claim 1, wherein the second analyzer emits an electron beam having an accelerating voltage in a range of about 0.5 kV to about 1.0 kV and a current condition in a range of about 1 pA to about 15 pA.

3. The method of claim 1, wherein the pretreating the sample further comprises combining the sample with a supporting substrate or the inert holder.

4. The method of claim 1, wherein the transporting the sample into the first analyzer comprises transporting the sample through a connection tube between the inert chamber and the first analyzer; and
    wherein the inert atmosphere of the inert chamber and the connection tube has moisture in a range of 0 ppm to about 0.1 ppm and oxygen in a range of 0 ppm to about 0.5 ppm.

* * * * *